(12) United States Patent
Nguyen et al.

(10) Patent No.: US 10,660,841 B2
(45) Date of Patent: *May 26, 2020

(54) COMPOSITIONS AND METHODS FOR TREATING HAIR

(71) Applicant: L'OREAL, Paris (FR)

(72) Inventors: Nghi Van Nguyen, Edison, NJ (US);
Jim Mitchell Singer, South Orange, NJ (US); Siliu Tan, Westfield, NJ (US);
Aditi Gogineni, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/854,872

(22) Filed: Dec. 27, 2017

(65) Prior Publication Data

US 2019/0192414 A1    Jun. 27, 2019

(51) Int. Cl.
   *A61Q 5/06*     (2006.01)
   *A61K 8/81*     (2006.01)
   *A61K 8/58*     (2006.01)

(52) U.S. Cl.
   CPC ............ *A61K 8/8152* (2013.01); *A61K 8/585* (2013.01); *A61Q 5/06* (2013.01)

(58) Field of Classification Search
   None
   See application file for complete search history.

(56) References Cited

U.S. PATENT DOCUMENTS

| | | | |
|---|---|---|---|
| 2010/0215609 A1* | 8/2010 | Knappe | A61K 8/8147 424/70.15 |
| 2010/0254932 A1 | 10/2010 | Benabdillah et al. | |
| 2011/0097278 A1* | 4/2011 | Verboom | A61Q 5/06 424/43 |
| 2012/0070391 A1 | 3/2012 | Schultze et al. | |
| 2013/0084256 A1* | 4/2013 | Li | A61K 8/37 424/59 |
| 2014/0076346 A1 | 3/2014 | Bourdin et al. | |
| 2014/0170105 A1* | 6/2014 | Chen | A61K 8/891 424/70.121 |
| 2016/0193135 A1 | 7/2016 | Pasquet et al. | |
| 2017/0135942 A1* | 5/2017 | Novack | A61K 8/88 |

FOREIGN PATENT DOCUMENTS

| | | |
|---|---|---|
| EP | 1321130 A2 | 6/2003 |
| EP | 2065023 A2 | 6/2009 |
| EP | 2065024 A2 | 6/2009 |
| EP | 2065028 A2 | 6/2009 |
| FR | 2924339 A1 | 6/2009 |
| FR | 2924341 A1 | 6/2009 |
| WO | 2015022259 A1 | 2/2015 |

* cited by examiner

*Primary Examiner* — Jyothsna A Venkat
(74) *Attorney, Agent, or Firm* — Polsinelli PC (L'Oreal USA)

(57) ABSTRACT

Disclosed herein are compositions suitable for styling hair. Certain compositions comprise
   a. at least one alkoxysilane having at least one solubilizing functional group and at least one amino substituent; and
   b. at least one carboxylic acid-containing latex film former.

The at least one alkoxysilane may be neutralized by the at least one carboxylic acid-containing latex film former. Also provided are method of using same.

7 Claims, No Drawings

COMPOSITIONS AND METHODS FOR TREATING HAIR

FIELD OF THE INVENTION

The disclosure relates to compositions for use on keratinous substances. In particular, it relates to compositions and methods for styling the hair.

BACKGROUND

Compositions for styling the hair are known, such as, for example, hair spray compositions, hair gels and mousses, hair volumizing compositions, hair smoothing creams, lotions, serums, oils, clays, etc. The goals of many hair styling compositions include holding or fixing the hair in a particular shape, imparting or increasing volume of the hair, smoothing the hair, and/or decreasing or eliminating the appearance of frizz.

Current products for styling the hair typically include water-soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, and often as the concentration of the polymer increases, its viscosity rapidly increases. In styling applications, as the solvent evaporates, the polymer solution becomes thicker on the hair surface, resulting in a sticky or tacky film. These products also tend to exhibit problems with product spreadability, hair manageability, and humidity resistance, which is especially a problem in hot and humid environments.

Particularly, while previous compositions comprising latex polymers may provide clean properties to the hair given its anionic nature, the clean properties can translate into difficult application and/or distribution of the product, quick absorption, dryness, and/or possibly static in the hair. The presence of film formers can also leave the hair with a stiff, crunchy, and/or sticky feel. Often, other ingredients and traditional silicones may be used in combination with latex polymers to overcome the brittleness and stiffness that may result from the use of latex polymers in hair compositions. However, this tends to make the hair feel greasy and oily and it can still be challenging for manufacturers to incorporate new ingredients into the compositions because this may negatively impact performance, certain cosmetic attributes, texture, and formulation stability. Alternative conditioning agents, such as non-ionic silicones and humectants, can actually plasticize the film produced by the product, thus affecting its high humidity curl retention, and creating build up, which weighs down the hair.

There is thus a need for new hair styling products which address one or more of these problems.

SUMMARY

One aspect of the invention pertains to a hair styling composition. In one or more embodiments, the composition comprises:
  a. at least one alkoxysilane having at least one solubilizing functional group and at least one amino substituent; and
  b. at least one carboxylic acid-containing latex film former.

In some embodiments, the at least one alkoxysilane comprises a compound of formula (I):

wherein:
$R_4$ is chosen from OR' groups;
$R_5$ is chosen from OR" groups;
$R_6$ is chosen from OR'" groups;
$R_1$, $R_2$ are chosen from hydrogen;
$R_3$, R', R", R'", which may be identical or different, are chosen from linear and branched, saturated and unsaturated hydrocarbon groups, optionally bearing at least one additional chemical group, wherein R', R", and R'" may also be chosen from hydrogen. In one or more embodiments, the at least one alkoxysilane comprises 3-aminopropyltriethoxysilane. In some embodiments, the at least one alkoxysilane is present in an amount of from about 0.01 to about 10% by weight of the total composition. In one or more embodiments, the at least one carboxylic acid-containing latex film former is selected from the group consisting of acrylates copolymer, polyacrylate-2 crosspolymer, styrene/acrylic copolymer, acrylates/hydroxyesters acrylates copolymer, styrene/acrylates copolymer, styrene/acrylates/ammonium methacrylate copolymer, acrylates/beheneth-25 methacrylate crosspolymer copolymer, acrylates/steareth-20-25 methacrylate crosspolymer copolymer, acrylic copolymer, polyacrylate-15 or mixtures thereof. In some embodiments, the at least one carboxylic acid-containing latex film former is present in an amount of from about 0.1 to about 20% by weight of the total composition. In one or more embodiments, the composition further comprises a nonionic latex film former. In some embodiments, the nonionic latex film former is selected from the group consisting of acrylates copolymer, polyacrylate-2 crosspolymer, styrene/acrylates copolymer, acrylates/ethylhexyl acrylate copolymer and combinations thereof. In one or more embodiments, the nonionic latex film former is present in an amount of from about 0.1 to about 10% by weight of the total composition. In some embodiments, the composition further comprises a plasticizer. In one or more embodiments, the composition does not further comprise an acid.

Another aspect of the invention pertains to hair styling composition comprising at least one alkoxysilane having at least one solubilizing functional group and at least one amino substituent at least partially neutralized with at least one carboxylic acid-containing latex film former.

In some embodiments, the at least one alkoxysilane comprises a compound of formula (I):

wherein:
$R_4$ is chosen from OR' groups;
$R_5$ is chosen from OR" groups;
$R_6$ is chosen from OR'" groups;
$R_1$, $R_2$ are chosen from hydrogen;
$R_3$, R', R", R'", which may be identical or different, are chosen from linear and branched, saturated and unsaturated hydrocarbon groups, optionally bearing at least one additional chemical group, wherein R', R", and R'" may also be chosen from hydrogen. In one or more embodiments, the at least one alkoxysilane comprises 3-aminopropyltriethoxysilane. In some embodiments, the at least one alkoxysilane is present in an amount of from about 0.01 to about 10% by weight of the total composition. In one or more embodiments, the at least one carboxylic acid-containing latex film former is selected from the group consisting of acrylates copolymer, polyacrylate-2 crosspolymer, styrene/acrylic copolymer, acrylates/hydroxyesters acrylates copolymer, styrene/acrylates copolymer, styrene/acrylates/ammonium methacrylate copolymer, acrylates/beheneth-25 methacrylate crosspolymer copolymer, acrylates/steareth-20-25 methacrylate crosspolymer copolymer, acrylic copolymer, polyacrylate-15 or mixtures thereof. In some embodiments, the at least one carboxylic acid-containing latex film former is present in an amount of from about 0.1 to about 20% by weight of the total composition. In one or more embodiments, the composition further comprises a nonionic latex film former. In some embodiments, the nonionic latex film former is selected from the group consisting of acrylates copolymer, polyacrylate-2 crosspolymer, styrene/acrylates copolymer, acrylates/ethylhexyl acrylate copolymer and combinations thereof. In one or more embodiments, the composition further comprises a plasticizer. In some embodiments, the composition does not further comprise an acid.

Another aspect of the invention pertains to a method of styling hair. In one or more embodiments, the method comprises any of the hair styling compositions described herein to hair. In some embodiments, the method further comprises shaping the hair.

It is to be understood that both the foregoing general description and the following detailed description present various embodiments of the disclosure, and are intended to provide an overview or framework for understanding the nature and character of the claims.

DETAILED DESCRIPTION

One aspect of the invention pertains to a hair styling composition comprising:
  a. at least one alkoxysilane having at least one solubilizing functional group and at least one amino substituent; and
  b. at least one carboxylic acid-containing latex film former.

In one or more embodiments, the alkoxysilane is at least partially neutralized with the at least one carboxylic acid-containing latex film former. It has been surprisingly discovered that the combination of alkoxysilanes, acid and carboxylic acid-containing latex film former provides good film adhesion, anti-frizz properties, and easy application for hair, while also providing the benefit of not requiring pre-neutralization of the alkoxysilane. While not wishing to be bound by any particular theory, it is thought that the alkoxysilane forms a complex with the carboxylic acid groups on the latex film former. After application of the composition to hair fiber, this complex condenses to form a larger and robust network. This robust film contains covalently-linked siloxane and ionically-linked film former and alkoxysilane.

Alkoxysilane

The hair styling compositions described herein comprise at least one alkoxysilane having at least one solubilizing functional group and at least one amino substituent. In one or more embodiments, the alkoxysilane is cationic. The cationic alkoxysilane may be neutralized by one or more acids present in the composition. In some embodiments, the composition may comprise more than one alkoxysilane. In further embodiments any additional alkoxysilanes are neutralizable. As used herein, "neutralizable" alkoxysilane means that the compound contains neutralizable moieties such as amine and thiol groups. In some embodiments, the additional alkoxysilanes may be non-neutralizable. As used herein, "non-neutralizable" alkoxysilane means that the alkoxysilane does not contain such neutralizable moieties.

The at least one alkoxysilane comprising at least one basic functional group that is present in the compositions disclosed herein, is chosen from organosilanes comprising one, two or three silicon atoms, such as one or two silicon atoms. They should also comprise at least one basic chemical function. The at least one basic chemical functional group may correspond to any function that confers a basic nature on the silicon compound, and is, for instance, an amine function such as a primary, secondary or tertiary amine function. The basic chemical function of the silicon compounds according to the present disclosure may optionally comprise other functions, such as, another amine function, an acid function or a halogen function.

The at least one alkoxysilane comprising at least one basic functional group that is present in the compositions according to the present disclosure, can also comprise at least two hydrolysable or hydroxyl groups per molecule. The hydrolysable groups are chosen, for example, from alkoxy, aryloxy and halogen groups. They may also optionally comprise other chemical functions such as acid functions.

According to at least one embodiment of the present disclosure, the at least one alkoxysilane comprising at least one basic functional group that is present in the compositions disclosed herein is chosen from the entities of formula (I):

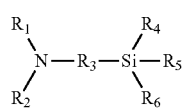

(I)

wherein:
$R_4$ is chosen from halogens, OR' and $R'_1$;
$R_5$ is chosen from halogens, OR" and $R'_2$;
$R_6$ is chosen from halogens, OR'" and $R'_3$;
$R_1$, $R_2$, $R_3$, R', R", R'", $R'_1$, $R'_2$ and $R'_3$ are each independently chosen from linear and branched, saturated and unsaturated hydrocarbon-based groups optionally bearing additional chemical groups such as acid or amine groups, it also being possible for $R_1$, $R_2$, R', R" and R'" to be hydrogens, and at least two of the $R_4$, $R_5$ and $R_6$ groups are different from the $R'_1$, $R'_2$ and $R'_3$ groups.

In at least one embodiment, the $R_1$, $R_2$, R', $R'_1$, $R'_2$, $R'_3$, R" and R'" groups are chosen from $C_1$-$C_{12}$ alkyl, $C_5$-$C_{14}$ aryl, $(C_1$-$C_8)$alkyl$(C_5$-$C_{14})$aryl and $(C_1$-$C_{14})$aryl$(C_1$-$C_8)$ alkyl radicals.

In at least one embodiment, the $R_3$ group is chosen from $C_1$-$C_{12}$ alkylene, optionally substituted with an amino group, $C_5$-$C_{14}$ arylene, $(C_1$-$C_8)$alkylene$(C_5$-$C_{14})$arylene and $(C_5$-$C_{14})$arylene$(C_1$-$C_8)$alkylene radicals.

According to another embodiment of the present disclosure, the at least one alkoxysilane comprising at least one basic functional group corresponding to the formulae (I) is chosen from, for instance, 3-aminopropyltriethoxysilane, 3-aminopropylmethyldiethoxysilane, N-(2-aminoethyl)-3-aminopropylltriethoxysilane and 3-(2-aminoethylamino) propylmethyldiethoxysilane.

According to another embodiment, the at least one alkoxysilane comprising at least one basic functional group that is used according to the present disclosure is chosen from the entities of formula (II):

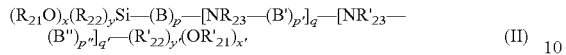 (II)

wherein:
$R_{21}$, $R_{22}$, $R'_{21}$ and $R'_{22}$ are each independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl and carbonyl groups,
x is an integer ranging from 1 to 3, y=3-x, x' is an integer ranging from 1 to 3, y'=3-x', p=0 or 1, p'=0 or 1, p"=0 or 1, q=0 or 1, q'=0 or 1, it being understood that at least q or q' is other than zero,
B, B' and B" are each independently chosen from linear and branched $C_1$-$C_{20}$ alkylene divalent radicals,
$R_{23}$ and $R'_{23}$ are each independently chosen from hydrogen atoms, and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_3$-$C_{20}$ alkyl ester, amine, amide, carboxyl, alkoxysilane, hydroxyl, carbonyl and acyl groups.

As explained above, $R_{21}$, $R_{22}$, $R'_{21}$, $R'_{22}$, $R_{23}$ and $R'_{23}$ are each independently chosen from hydrocarbon-based chains. As used herein, "hydrocarbon-based chain" is intended to mean a chain containing 1 to 30 carbon atoms, such as 1 to 10 carbon atoms.

In at least one embodiment, the aromatic ring contains from 6 to 30 carbon atoms, for example, an optionally substituted phenyl radical.

According to at least one embodiment, $R_{21}$=$R'_{21}$; $R_{22}$=$R'_{22}$; x=x'; y=y'; p=p'; B=B'; q=1 and q'=0.

In at least one embodiment, the at least one alkoxysilane comprising at least one basic functional group is chosen from the entities of formula (II), wherein:
$R_{21}$, $R_{22}$, $R'_{21}$ and $R'_{22}$, which may be identical or different, are chosen from $C_1$-$C_4$ alkyl groups,
p=p'=1;
B and B', which may be identical or different, are chosen from linear $C_1$-$C_4$ alkylene groups, and
$R_{23}$ is hydrogen.

For example, the at least one alkoxysilane comprising at least one basic functional group may comprise a substituent comprising a secondary amine function, such as the bis[3-(triethoxysilyl)propyl]amine of formula $(CH_3CH_2O)_3$—Si$(CH_2)_3NH(CH_2)_3Si(OCH_2CH_3)_3$ proposed by the company Fluorochem, the bis[trimethoxysilylpropyl]amine of formula $(CH_3O)_3$—Si$(CH_2)_3NH(CH_2)_3Si(OCH_3)_3$ proposed by the company Gelest, the bis[methyldiethoxysilylpropyl] amine of formula $(CH_3CH_2O)_2CH_3Si(CH_2)_3NH(CH_2)_3SiCH_3(OCH_2CH_3)_2$ proposed by the company Gelest and the bis[3-trimethoxysilylpropyl]ethylenediamine of formula $(CH_3O)_3Si(CH_2)_3NH(CH)_2NH(CH_2)_3Si(OCH_3)_3$ proposed by the company Gelest. In at least one embodiment of the present disclosure, bis[3-(triethoxysilyl)propyl]amine and bis[methyldiethoxysilylpropyl]amine are used.

According to another embodiment of the present disclosure, the at least one alkoxysilane comprising at least one basic functional group is chosen from the entities of formula (III):

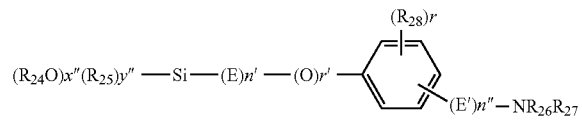 (III)

wherein:
$R_{24}$ and $R_{25}$ are each independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl and carbonyl groups,
x"=2 or 3;
y"3-x";
n'=0 or 1; and
n"=0 or 1;
E and E' are each independently chosen from linear and branched $C_1$-$C_{20}$ alkylene divalent radicals,
$R_{26}$ and $R_{27}$ are each independently chosen from a hydrogen atom and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups,
r is an integer ranging from 0 to 4,
r'=0 or 1, and
each instance of $R_{28}$ is independently chosen from a hydrogen atom and linear and branched, saturated and unsaturated, $C_1$-$C_{10}$, hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups.

As explained above, $R_{24}$, $R_{25}$' $R_{26}$ and $R_{27}$ are each independently chosen from hydrocarbon-based chains. As used herein, "hydrocarbon-based chain" is intended to mean a chain containing from 1 to 30 carbon atoms, such as containing from 1 to 10 carbon atoms.

In at least one embodiment, the aromatic ring contains from 6 to 30 carbon atoms, for example an optionally substituted phenyl radical.

The at least one alkoxysilane comprising at least one basic functional group of formula (III), may be chosen wherein:
$R_{24}$ is a $C_1$-$C_4$ alkyl,
x"=3, n'=n"=1; r=r'=0, and
$R_{26}$ and $R_{27}$ are each independently chosen from a hydrogen atom and groups chosen from $C_1$-$C_4$ alkyl, $C_1$-$C_4$ hydroxyalkyl and $C_1$-$C_4$ aminoalkyl groups.

In at least one embodiment, the at least one alkoxysilane comprising at least one basic functional group of formula (III), may be chosen from, for example:

3-(m-aminophenoxy)propyltrimethoxysilane, of formula:

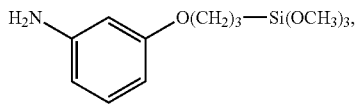

p-aminophenyltrimethoxysilane, of formula:

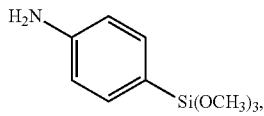

and
N-(2-aminoethylaminomethyl)phenethyltrimethoxysilane, of formula:

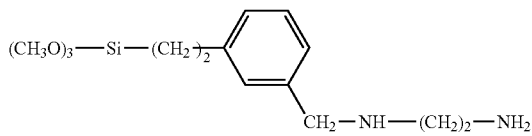

In another embodiment, the at least one alkoxysilane comprising at least one basic functional group may comprise at least one primary or secondary amine function.

In yet another embodiment, the at least one alkoxysilane comprising at least one basic functional group that can be used in the compositions disclosed herein, correspond to formula (I):

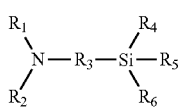

wherein:
$R_1$ and $R_2$, are each independently chosen from a hydrogen atom and ethyl, propyl and aminoethyl groups;
$R_3$ is chosen from ethyl, propyl and methylphenethyl groups;
$R_4$, $R_5$ and $R_6$ are each independently chosen from methyl, methoxy and ethoxy groups.

Non-limiting examples of the at least one alkoxysilane of formula (I) include, but are not limited to: 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and N-(2-aminoethylaminomethyl)phenethyltrimethoxysilane of formula:

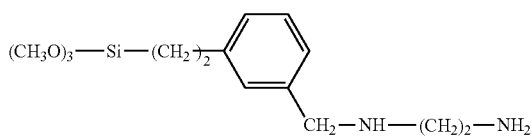

In one or more embodiments, the alkoxysilane is present in an amount of from about 0.1, 0.2, 0.3, 0.4, 0.5 to about 0.5, 0.6, 0.7, 0.8, 0.9, 1, 2, 3, 4 or 5 wt. % of the total composition.

Latex Film Former

The compositions according to the disclosed embodiments comprise at least one carboxylic acid-containing latex polymer, wherein at least one latex polymer is a film-forming polymer. Said carboxylic acid-containing latex polymers may be ionic (i.e., anionic) or amphoteric. Said amphoteric latex polymer will include cationic and anionic groups, but the overall charge may be either anionic or cationic. In some embodiments, the composition further comprise at least one nonionic latex polymer. In one or more embodiments, the composition further comprises at least one cationic latex polymer.

In one or more embodiments, the carboxylic acid-containing latex polymer is present in an amount of about 0.1, 0.2, 0.3, 0.4, 0.5, 1, 2.5, 2, 2.5, 3, 3.5, 4, 4.5 to about 2, 3, 4, 5, 6, 7, 8, 9, 10, 15 or 20 wt. % by weight of the total composition. In embodiments where the composition also comprises a nonionic latex film former, the nonionic latex film former is present in an amount of about 0.1, 0.2, 0.3, 0.4, 0.5, 1, 2.5, 2, 2.5, 3, 3.5, 4, 4.5 to about 2, 3, 4, 5, 6, 7, 8, 9, 10, 15 or 20 wt. % by weight of the total composition.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at or below ambient temperature, or in other words, will only form a film at temperatures above ambient. For purposes of this disclosure, ambient temperature is below about 40° C., such as ranging from about 15° C. to about 30° C.

In various embodiments, the latex polymer may be provided in the form of aqueous dispersions prior to formulating the compositions of the disclosure. In other embodiments, the aqueous dispersions may be obtained through an emulsion polymerization of monomers wherein the resulting latex polymers have a particle size less than about 1 μm. In certain other embodiments, a dispersion prepared by the polymerization in water of one or more monomers having a polymerizable double bond may be chosen. In other embodiments, the latex polymers are produced from condensation reactions between monomers and subsequently dispersed in an aqueous medium.

In various embodiments, the latex polymers may exist as dispersed polymer particles in a dispersion medium, such as an aqueous dispersion medium. In other embodiments, the latex polymers may be dispersed in independent dispersion media. In further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at about 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol or isopropanol; polyols, including glycols, such as those containing from about 2 to 8 carbon atoms, for example propylene glycol, ethylene glycol, 1,3-butylene glycol, dipropylene glycol, hexylene glycol, or glycerin; hydrocarbons, for example, isododecane or mineral oil; or silicones, for example dimethicones, cyclic dimethicones (INCI name: cyclomethicones), or cyclopentasiloxane; or mixtures thereof.

In other embodiments, the solvent of the dispersion medium comprises water. In other embodiments, the solvent of the dispersion medium comprises water and at least one cosmetically acceptable organic solvent. In further embodiments, the solvent comprises water. In further embodiments, the solvent of the dispersion medium primarily consists essentially of water. For example, the solvent of the dispersion medium may, in at least certain exemplary embodiments, comprise greater than about 50% water, greater than about 55% water, greater than about 60% water, greater than about 65% water, greater than about 70% water, greater than about 75% water, greater than about 80% water, greater than about 85% water, greater than about 90% water, greater than about 95% water, greater than about 96% water, greater than about 97% water, greater than about 98% water, or greater than about 99% water.

In various embodiments, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In certain embodiments, latex particles according to the disclosure may have an average diameter ranging up to about 1000 nm, from about 50 nm to about 800 nm, or from about 100 nm to about 500 nm. Such particle sizes may be measured with a laser granulometer (e.g. Brookhaven B190).

In certain embodiments, the latex polymers may be chosen from acrylate latex polymers, such as those resulting from the homopolymerization or copolymerization of monomers chosen from (meth)acrylics, (meth)acrylates. The term "(meth)acryl" and variations thereof, as used herein, means acryl or methacryl.

In certain embodiments, the (meth)acrylic monomers may be chosen from acrylic acid, methacrylic acid, citraconic acid, itaconic acid, maleic acid, fumaric acid, crotonic acid, maleic anhydride, or mixtures thereof.

In certain embodiments, the (meth)acrylic monomers may be chosen from C1-C8 alkyl (meth)acrylic, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth) acrylic, octyl (meth)acrylic, isooctyl (meth)acrylic, or mixtures thereof.

In certain embodiments, the esters of (meth)acrylic monomers may be chosen from C1-C8 alkyl (meth)acrylate, methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, or combinations thereof.

In certain embodiments, the esters of (meth)acrylic monomers may be chosen from C1-C8 alkoxy (meth)acrylate, methoxy (meth)acrylate, ethoxy (meth)acrylate, propyl oxide (meth)acrylate, isopropyl oxide (meth)acrylate, butyl oxide (meth)acrylate, tert-butyl oxide (meth)acrylate, pentyl oxide (meth) acrylate, isopentyl oxide (meth)acrylate, neopentyl oxide (meth)acrylate, C2-C6 hydroxy alkyl (meth) acrylates, hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth) acrylate, aryl (meth)acrylates benzyl (meth)acrylate, phenyl (meth)acrylate, or mixtures thereof.

In certain embodiments, the esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, N,N,N-trimethylaminoethyl (meth)acrylate, salts of the ethylenic amines, or silicone macromonomers.

In certain embodiments, the amides of (meth)acrylic monomers can, for example, be made of (meth)acrylamide, N-alkyl (meth)acrylamides, N—(C1-C12) alkyl (meth)acrylates such as N-ethyl (meth)acrylamide, N-t-butyl (meth) acrylamide, N-t-octyl (meth)acrylamide, N-methylol (meth) acrylamide, N-diacetone (meth)acrylamide, or mixtures thereof.

In certain embodiments, the vinyl monomers can include, but are not limited to, vinyl cyanide compounds such as acrylonitrile or methacrylonitrile; vinyl esters such as vinyl formate, vinyl acetate, vinyl propionate, vinyl neodecanoate, vinyl pivalate, vinyl benzoate, vinyl t-butyl benzoate, or triallyl cyanurate; vinyl halides such as vinyl chloride or vinylidene chloride; aromatic mono- or divinyl compounds such as styrene, α-methylstyrene, chlorostyrene, alkylstyrene, divinylbenzene or diallyl phthalate; or mixtures thereof. In other embodiments, the vinyl monomers can include include para-styrensulfonic, vinylsulfonic, 2-(meth) acryloyloxyethylsulfonic, or 2-(meth)acrylamido-2-methyl-propylsulfonic acids.

The list of monomers given is not limiting, and it should be understood that it is possible to use any monomer known to those skilled in the art which includes acrylic and/or vinyl monomers (including monomers modified with a silicone chain).

In certain embodiments, silicone acrylic polymers may also optionally be used as vinyl polymer in at least one exemplary and non-limiting embodiment.

In other embodiments, one of the at least two latex polymers may be chosen from polyurethane latex polymers, such as aqueous polyurethane dispersions comprising the reaction products of (i), (ii), and/or (iii), defined below.

Reaction product (i) may be any prepolymer according to the formula:

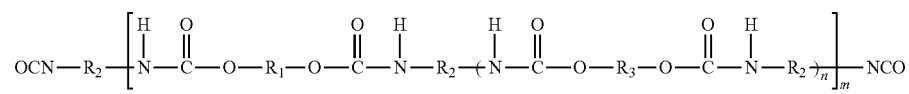

wherein $R_1$ is chosen from bivalent radicals of a dihydroxyl functional compound, $R_2$ is chosen from hydrocarbon radicals of an aliphatic or cycloaliphatic polyisocyanate, $R_3$ is chosen from radicals of a low molecular weight diol, optionally substituted with ionic groups, n ranges from about 0 to about 5, and m is greater than about 1.

Suitable dihydroxyl compounds for providing the bivalent radical $R_1$ include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, or polyhydroxy polycarbonates may be chosen. Mixtures of such compounds are also within the scope of the disclosure.

In some embodiments, the polyester diol may optionally be prepared from aliphatic, cycloaliphatic, or aromatic dicarboxylic or polycarboxylic acids, or anhydrides thereof; or dihydric alcohols such as diols chosen from aliphatic, alicyclic, or aromatic diols.

In other embodiments, the aliphatic dicarboxylic or polycarboxylic acids may be chosen from succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic, trimellitic acid, or mixtures thereof.

In various embodiments, the acid anhydrides may be chosen from o-phthalic, trimellitic, succinic acid anhydride or mixtures thereof. In another embodiment, the dicarboxylic acid may be adipic acid.

In certain embodiments, the dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, or mixtures thereof. In other embodiments, the cycloaliphatic and/or aromatic dihydroxyl compounds may also be suitable as the dihydric alcohol(s) for the preparation of the polyester polyol(s).

In certain embodiments, the polyester diols may be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, for example difunctional, starter molecules such as, for example, the dihydric alcohols mentioned above. In some embodiments, the corresponding polymers of ε-caprolactone may be chosen.

In certain embodiments, the polyester polyol, for example polyester diol, radical $R_1$, may be obtained by polycondensation of dicarboxylic acids, such as adipic acid, with polyols, for example diols, such as hexanediol, neopentyl glycol, or mixtures thereof.

In certain embodiments, the polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

In certain embodiments, optional polyether polyols may be obtained in any known manner by reacting starting compounds which contain reactive hydrogen atoms with alkylene oxides, such as ethylene oxide; propylene oxide; butylene oxide; styrene oxide; tetrahydrofuran; epichlorohydrin, or mixtures thereof. In certain embodiments, the polyethers do not contain more than about 10% by weight of ethylene oxide units. In other embodiments, polyethers obtained without addition of ethylene oxide may be chosen.

In other embodiments, polyethers modified with vinyl polymers may be chosen. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536, all incorporated by reference herein.

In certain embodiments, the polythioethers may be chosen from condensation products obtained from thiodiglycol per se and/or with other glycols, dicarboxylic acids, formaldehyde, aminocarboxylic acids, and/or amino alcohols. In other embodiments, the products obtained are either mixed polythioethers, polythioether esters, or polythioether ester amides, depending on the co-components.

In certain embodiments, the polyacetals may be chosen from compounds which can be prepared from aldehydes, such as formaldehyde, and from glycols, such as diethylene glycol, triethylene glycol, ethoxylated 4,4'-(dihydroxy)diphenyl-dimethylmethane, or (1,6)-hexanediol. Polyacetals according to various non-limiting embodiments of the disclosure can also be prepared by polymerization of cyclic acetals.

In certain embodiments, optional polyhydroxy polyesteramides and polyamines include, for example, the mainly linear condensation products obtained from saturated or unsaturated, polybasic carboxylic acids or anhydrides thereof; from saturated or unsaturated, polyvalent amino alcohols; from diamines; from polyamines; or mixtures thereof.

In certain embodiments, optional monomers for the production of polyacrylates having hydroxyl functionality include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, or 2-isocyanatoethyl methacrylate.

In certain embodiments, mixtures of dihydroxy compounds may be chosen.

In various embodiments, optional polyisocyanates for providing the hydrocarbon-based radical $R_2$ include, for example, organic diisocyanates having a molecular weight ranging from about 100 to about 1500, from about 112 to about 1000, or from about 140 to about 400.

In other embodiments, optional diisocyanates are chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates include tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane, 1,4-bis(isocyanatomethyl)cyclohexane, bis(4-isocyanato-3-methylcyclohexyl)methane, or mixtures thereof.

In certain embodiments, the diisocyanates are chosen from aliphatic or cycloaliphatic diisocyanates, for example, 1,6-hexamethylene diisocyanate, isophorone diisocyanate, dicyclohexylmethane diisocyanate, or mixtures thereof.

In some embodiments, the use of diols, for example low molecular weight diols, $R_3$, may allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain embodiments, the compounds contain only aliphatic groups. In other embodiments, the diols may have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)propane), or mixtures thereof.

In other embodiments, the low molecular weight diols may contain ionic or potentially ionic groups. Suitable low molecular weight diols containing ionic or potentially ionic groups may be chosen from those disclosed in U.S. Pat. No. 3,412,054, incorporated by reference herein. In various embodiments, compounds may be chosen from dimethylolbutanoic acid (DMBA), dimethylolpropionic acid (DMPA), or carboxyl-containing caprolactone polyester diol. If low molecular weight diols containing ionic or potentially ionic groups are chosen, they may be used in an amount such that less than about 0.30 meq of —COOH is present per gram of polyurethane in the polyurethane dispersion. In certain embodiments, the low molecular weight diols containing ionic or potentially ionic groups are not used.

Reaction product (ii) may be chosen from at least one chain extender according to the formula:

$$H_2N-R4-NH_2$$

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine or piperazine; and alkylene oxide diamines such as dipropylamine diethylene glycol (such as DPA-DEG sold by the company Tomah Products), 2-methyl-1,5-pentanediamine (such as Dytec A sold by the company DuPont), hexanediamine, isophoronediamine, and 4,4-methylenedi(cyclohexylamine), and the DPA-series of ether amines available from the company Tomah Products, including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol, dipropylamine cyclohexane-1,4-dimethanol, or mixtures thereof.

Reaction product (iii) may be chosen from at least one chain extender according to the formula:

$$H_2N-R5-NH_2$$

wherein R5 is chosen from alkylene radicals substituted with ionic or potentially ionic groups. In certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, or sulphonate groups. At least partial conversion of the groups convertible into salt groups of the type mentioned may take place before or during the mixing with water. Specific compounds include diaminosulphonates, for example the sodium salt of N-(2-aminoethyl)-2-aminoethanesulphonic acid (AAS) or the sodium salt of N-(2-aminoethyl)-2-aminopropionic acid.

In certain embodiments, R5 represents an alkylene radical substituted with sulphonic acid or sulphonate groups. By way of example only, the reaction product (iii) is chosen from sodium salts of N-(2-aminoethyl)-2-aminoethanesulphonic acid.

In various embodiments according to the disclosure, it may be possible to choose a polymer that comprises both acrylate and polyurethane parts at the molecular level.

In certain embodiments, carboxylic acid-containing latex polymers may be chosen from aqueous dispersions of the following ionic latex polymers containing acrylic acid:

| Latex | INCI Name | Sold By |
|---|---|---|
| Anionic Containing Acrylic Acid Groups ||| 
| LUVIFLEX Soft | Acrylates copolymer | BASF |
| FIXATE Superhold | Polyacrylate-2 Crosspolymer | Lubrizol |
| NEOCRYL A-1120 | Styrene/Acrylic copolymer | DSM |
| ACULYN 33 | Acrylates Copolymer | Dow Chemical |
| LUVIMER MAE | Acrylates copolymer | BASF |
| BALANCE CR | Acrylates copolymer | Akzo Nobel |
| ACUDYNE DHR | Acrylates/hydroxyesters Acrylates Copolymer | Dow Chemical |
| ACUDYNE 180 POLYMER | Acrylates/Hydroxyesters Acrylates Copolymer | Dow Chemical |
| ACUDYNE SHINE | Styrene/Acrylates Copolymer | Dow Chemical |
| ACUDYNE BOLD | Styrene/Acrylates Copolymer | Dow Chemical |
| JONCRYL 77 | Styrene/Acrylates Copolymer | BASF |
| SYNTRAN PC5620 CG | Styrene/Acrylates/Ammonium Methacrylate Copolymer | Interpolymer |
| SYNTRAN 5009-CG | Styrene/Acrylates/Ammonium Methacrylate Copolymer | Interpolymer |
| SYNTRAN 5190-CG | Acrylates Copolymer | Interpolymer |
| SYNTRAN 5760-CG | Styrene/Acrylates/Ammonium Methacrylate Copolymer | Interpolymer |
| SYNTRAN 5620 | Styrene/Acrylates/Ammonium Methacrylate Copolymer | Interpolymer |
| SYNTRAN 5762 | Styrene/Acrylates/Ammonium Methacrylate Copolymer | Interpolymer |
| SYNTRAN 5288 | Ethylene/acrylic acid copolymer (and) styrene/acrylates copolymer (and) c11-15 pareth-40 (and) c11-15 pareth-7 (and) sodium laureth-12 sulfate | Interpolymer |

-continued

| Latex | INCI Name | Sold By |
| --- | --- | --- |
| SYNTRAN PC5208 | Polyacrylate-15 | Interpolymer |
| ACULYN 28 | Acrylates/Beheneth-25 Methacrylate Crosspolymer Copolymer | Dow Chemical |
| ACULYN 88 | Acrylates/Steareth-20-25 Methacrylate Crosspolymer Copolymer | Dow Chemical |
| DERMACRYL AQF | Acrylic Copolymer | Akzo Nobel |
| DAITOSOL 5500 GM | Acrylates/Ethylhexyl Acrylate copolymer | Kobo Products Inc. |
| DAITOSOL 3000 SLPN | Acrylates Copolymer | Kobo Products Inc. |
| DAITOSOL 3000VP3 | Acrylates Copolymer | Kobo Products Inc. |
| DAITOSOL 5000 PO | Acrylates/Ethylhexyl Acrylate copolymer | Kobo Products Inc. |
| DAITOSOL U9-40 GM | Polyurethane-1, Acrylates Copolymer | Kobo Products Inc. |
| Amphoteric Containing Acrylic Acid Groups | | |
| SYNTRAN PC5330 | Polyquaternium-91 (and) Polyacrylate-15 | Interpolymer |
| SYNTRAN PC5500 | Polyquaternium-91 (and) Polyacrylate-15 | Interpolymer |
| SYNTRAN PC5100-CG | Polyacrylate-21 (and) Acrylates/Dimethylaminoethyl Methacrylate copolymer | Interpolymer |
| SYNTRAN PC5775 | Acrylates/ethylhexyl acrylate/hema copolymer (and) acrylates/diethylaminoethyl methacrylate/ethylhexyl acrylate copolymer (and) isodeceth-6 (and) caprylyl glycol (and) sodium laureth sulfate | Interpolymer |
| SYNTRAN PC5227 CG | Polyacrylate-15 (and) polyacrylate-17 (and) butylene glycol | Interpolymer |

In some embodiments, the hair styling compositions described herein may further comprise a nonionic latex polymer. In one or more embodiments, the nonionic latex polymer may be chosen from:

| Latex | INCI Name | Sold By |
| --- | --- | --- |
| DAITOSOL 5000 AD | Acrylates copolymer | Kobo Products Inc. |
| DAITOSOL 5000 SJ | Polyacrylate-2 Crosspolymer | Kobo Products Inc. |
| DAITOSOL 5000 STY | Styrene/Acrylates Copolymer | Kobo Products Inc. |
| DAITOSOL 4000 SJT | Acrylates/Ethylhexyl Acrylate Copolymer | Kobo Products Inc. |

Coalescing Agents and Plasticizers

The compositions according to the disclosed embodiments may optionally comprise at least one component chosen from coalescing agents and plasticizers. Without wishing to be bound by theory, it is believed that the addition of coalescing agents and/or plasticizers may lower the glass transition temperature (Tg), decrease the Young's modulus, and/or increase the strain of latex polymers and/or the films formed by latex polymers. Further, the at least one coalescing agent and/or plasticizer may also be used to aid coating formation of the latex film to form a continuous and homogeneous film or coating and to improve adhesion. While the lowering of the Tg of the latex polymers can result in a softening of the film or coating formed by the latex polymers, it has been found that the coating or film produced on hair treated with the compositions of the disclosure imparts a stronger styling hold to the hair and a more balanced coating or film.

In various embodiments, the coalescing agents and/or plasticizers may be chosen from glycols and their derivatives, such as glycol ethers, for example, ethylene glycol, propylene glycol, diethylene glycol ethyl ether, diethylene glycol methyl ether, diethylene glycol butyl ether, diethylene glycol hexyl ether, diethylene glycol dibutyl ether, ethylene glycol methyl ether, ethylene glycol ethyl ether, ethylene glycol butyl ether, or ethylene glycol hexyl ether; glycol esters, such as diethylene glycol butyl ether acetate, propylene glycol dibenzoate or dipropylene glycol dibenzoate; cellulose esters, such as sucrose acetate; propylene glycol derivatives, such as propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, or propylene glycol butyl ether.

In other embodiments, the coalescing agents and/or plasticizers may be chosen from acid esters, such as carboxylic acid esters. In other embodiments, the component chosen from coalescing agents and plasticizers may be chosen from acetates, such as glycerol triacetate; citrates, such as triethyl citrate, tributyl citrate, triethyl acetylcitrate, tributyl acetylcitrate, or tri(2-ethylhexyl)acetylcitrate; phthalates, such as diethyl phthalate, dibutyl phthalate, dioctyl phthalate, dipentyl phthalate, dimethoxyethyl phthalate, butyl phthalate, or 2-ethylhexyl phthalate; phosphates, such as tricresyl phosphate, tributyl phosphate, triphenyl phosphate, or tributoxyethyl phosphate; tartrates, such as dibutyl tartrate; or sebacates, such as dimethyl sebacate or dibutyl sebacate.

In other embodiments, the coalescing agents and/or plasticizers may be chosen from, fatty acid esters, such as adipic acid esters, for example, diisobutyl adipate or diethyl adipate; stearic acid esters, such as ethyl stearate; or palmitic acid esters, such as 2-ethylhexyl palmitate, succinates, abietates, caprylates, caproates, enanthates, or myristates.

In further embodiments, the coalescing agents and/or plasticizers may be chosen from carbonates, such as ethylene carbonate or propylene carbonate; benzyl benzoate, sucrose benzoate, butyl acetylricinoleate, glyceryl acetylricinoleate, butyl glycolate, camphor, N-ethyl-o,p-toluenesulphonamide, or ethyl tosylamide.

In further embodiments, the coalescing agents and/or plasticizers may be chosen from compounds comprising at least one fatty acid chosen from caprylic acid, capric acid, lauric acid, myristic acid, palmitic acid, stearic acid, oleic acid, ricinoleic acid, linoleic acid, linolenic acid, arachidic acid, gadoleic acid, behenic acid, erucic acid, brassidic acid, cetoleic acid, lignoceric acid, or nervonic acid.

In further embodiments, the coalescing agents and/or plasticizers may be chosen from alcohols such as hexanol or benzyl alcohol.

In preferred embodiments, the coalescing agents and/or plasticizers may be chosen from propylene glycol dibenzoate, sold under the tradename Lexfeel® Shine by the company Inolex, dipropylene glycol dibenzoate, sold under the tradename Dermol DPG-2b by the company Alzo, and propylene glycol butyl ether, sold under the tradename Dowanol™ PnB by the company Dow Chemical.

It should be understood that mixtures of the above agents may be used according to various embodiments.

In various embodiments, the at least one component chosen from coalescing agents and plasticizers may be present in an amount ranging from about 0.1% to about 20% by weight, from about 0.1% to about 10% by weight, or from about 0.1% to about 5% by weight, with respect to the total weight of the composition.

In various embodiments, the at least one component chosen from coalescing agents and plasticizers may be present in an amount ranging from about 0.1% to about 2% by weight or from about 0.1% to about 1% by weight, with respect to the total weight of the composition.

In other embodiments, compositions of the disclosure may comprise at least one water-soluble resin such as polyethylene oxide having a molecular weight ranging from about 100,000 to about 10,000,000. Examples of such polyethylene oxides include, but are not limited to, Polyox water-soluble resins manufactured by the company Dow under the INCI names of PEG-2M, PEG-5M, PEG-7M, PEG-14M, PEG-23M, PEG-45M, PEG-90M, PEG-160M, and PEG-180M. PEG-90M is known under the tradename Polyox™ WSR 301 and PEG-45M is known under the tradename Polyox™ WSR 60k. The amounts of water-soluble resins in the compositions, when present, may range from about 0.1% to about 2% by weight, relative to the total weight of the composition.

Solvent

In addition to a solvent chosen from water, the compositions according to the disclosed embodiments may further comprise at least one cosmetically acceptable organic solvent. In certain embodiments, the at least one solvent in the compositions of the invention may be chosen from water, at least one cosmetically acceptable organic solvent, or a mixture of water and at least one cosmetically acceptable organic solvent. The cosmetically acceptable organic solvent may be chosen from volatile or non-volatile organic solvents.

In various embodiments, the cosmetically acceptable organic solvents may be water-miscible, e.g. a mixture capable of forming at 25° C. a homogeneous mixture that is transparent, or substantially transparent, to the eye, chosen from lower monoalcohols, such as those containing from about 1 to 5 carbon atoms, for example ethanol or isopropanol; polyols, including glycols, such as those containing from about 2 to 8 carbon atoms, for example propylene glycol, ethylene glycol, 1,3-butylene glycol, dipropylene glycol, pentylene glycol, hexylene glycol, glycerin, ethylhexylglycerin; hydrocarbons, such as, for example, isododecane or mineral oil; silicones, such as dimethicones, trisiloxanes, cyclomethicones, or cyclopentasiloxane; or mixtures thereof.

In some embodiments, the cosmetically acceptable organic solvent is chosen from propylene glycol, glycerin, ethylhexylglycerin, trisiloxane, dimethicone, isododecane, mineral oil, or mixtures thereof.

In certain embodiments, the latex polymer particles are not soluble in the solvent of the composition, and thus remain in particulate form while in the composition and after evaporation of the solvent. For example, in embodiments where the composition comprises alcohol as a cosmetically acceptable organic solvent, the latex particles may remain in particulate form upon evaporation of the alcohol, such as once the composition is applied to a substrate.

According to various embodiments, the at least one solvent may be present in an amount ranging up to about 95% by weight, from about 1% to about 90% by weight, or from about 5% to about 80% by weight, relative to the total weight of the composition.

Additional Components

The compositions according to the disclosed embodiments may further comprise additional components that are typically used in hair cosmetic compositions. Such components are known to those of skill in the art, or are within the ability of those of skill in the art to determine depending on the particular application, such as, for example, aminofunctional silicones, alkylpolyglucosides, anionic surfactants, cationic surfactants, cationic polymers, organic amines, carbonate compounds, emulsifying agents, fillers, pigments, conditioning agents, moisturizing agents, shine agents, sequestering agents, fragrances, preservatives, pH modifiers/neutralizing agents, stabilizers, salts, or mixtures thereof.

In one or more embodiments, the hair styling composition does not further comprise an acid (i.e., other than the acidity provided by the carboxylic acid groups on the latex film former). In some embodiments, such acids may include mineral or organic acids, such as hydrochloric acid, orthophosphoric acid, sulfuric acid, sulfonic acids, and carboxylic acids. Examples of carboxylic acids, include, for instance, acetic acid, tartaric acid, citric acid, and lactic acid. In some embodiments, such acids may be selected from the group consisting of lactic acid, phosphoric acid, orthophosphoric, citric acid, pyruvic acid, malic acid, hydrochloric acid or sulfuric acid, sulfonic acid and mixtures thereof.

In various embodiments, the composition described herein may have a pH ranging from about 3 to about 10, such as about 4 to about 8, or about 6 to about 7.

Methods of Preparation

Another aspect of the invention pertains to a method of preparing the compositions described herein. In some embodiments, the method comprises mixing the at least one alkoxysilane having at least one solubilizing functional group and at least one amino substituent with at least one acid, and at least one ionic latex film former. In one or more embodiments, the order of mixing the ingredients does not matter.

Methods of Use

In some embodiments, the compositions are in the form of hair styling compositions, in any form, such as, for example, a gel, an oil-gel, a lotion, an emulsion, or a liquid that may be sprayed onto or otherwise applied to the hair. In certain exemplary embodiments, the composition is provided in the form of a cream, mousse, or a spray.

In various embodiments, the composition is a hair styling or a hair care composition that provides styling or shaping benefits to the hair (e.g., styling hold, straightening, curling, curl definition). In other embodiments, the hair styling or hair care composition provides manageability benefits to hair (e.g., anti-frizz, smoothing, softness, conditioning). According to various embodiments, by "hair styling composition" or by "hair care composition", the composition is meant to be applied to hair on the head other than eyelashes and/or eyebrows. Hair styling and hair care compositions and mascaras are sometimes distinguishable based on the components of the compositions and/or the effects of the compositions when applied. In some embodiments, at least one component of a hair styling composition is not compatible for use in a mascara. In other embodiments, at least one component of a mascara is not compatible for use in a hair styling or hair care composition.

According to some embodiments, the composition is not applied to the eyelashes and/or eyebrows. In certain embodiments, the composition is not a mascara.

In certain embodiments, the composition may be applied to the hair by first applying to the hands, and then contacting the hair with the hands. In other embodiments, the composition may be applied directly onto the hair, such as by spraying. In other embodiments, the composition may be applied to wet or dry hair. The compositions may, in various embodiments, be applied to the hair as a leave-on treatment.

Also disclosed herein are methods for styling the hair, said methods comprising applying a composition according to the disclosure to the hair, either before, during, or after styling the hair. One or more steps of treating the hair with an external stimulus, such as heat, before, during, or after the composition has been applied to the hair are also contemplated. Additional methods comprise applying a composition according to disclosure to dry hair to achieve a desired shape.

In one or more embodiments, the hair is allowed to air dry after application of the composition, and no heat is applied to the hair. In some embodiments, the hair is allowed to air dry after application of the composition, and is styled or shaped with no heat being applied to the hair.

Styling or shaping the hair may involve the use of devices on hair such as a brush, a comb or running the fingers of the hand through the hair.

In one embodiment, the application of an external stimuli, such as heat, may be part of the hair styling process. By way of example only, before, during, or after the composition is applied to wet or dry hair, the hair may optionally be further treated with an external stimulus, for example with heat ranging from about 25° C. to about 250° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. The heating tools can generate heat through electrical current or heating lamps. Depending upon the desired style, these tools include, but are not limited to, heaters, blow dryers, flat irons, hot combs, hot curler sets, heated crimpers, heated wands/brushes, and hood driers or their combinations thereof.

Also disclosed herein are methods of imparting frizz control an comprising applying a composition according to the disclosure to the hair.

It should be noted, however, that compositions and films, as well as hair to which the composition or film has been applied, according to the disclosure may not have one or more of the herein-referenced properties, yet are intended to be within the scope of the disclosure.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a surfactant" is intended to mean at least one surfactant unless the context clearly indicates otherwise.

It should be understood that all patents and published patent applications referenced are incorporated herein in their entireties.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

It should be understood that compositions according to various embodiments of the disclosure form a film when applied to a substrate. However, the various properties of the film described herein are intended to include any film provided by compositions according to the disclosure, regardless of whether the film is attached or bonded to the substrate or not. By way of example only, once the compositions are applied to a substrate and a film is formed, the film may subsequently be removed in order to evaluate properties such as strain and Young's modulus.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. For example, the term "about" can mean within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It is understood that when an amount of a component is given, it is intended to signify the amount of the active material, unless otherwise indicated.

The compositions and methods according to the present disclosure can comprise, consist of, or consist essentially of the elements and limitations described herein, as well as any additional or optional ingredients, components, or limitations described herein or otherwise known in the art.

EXAMPLES

The following Examples are intended to be non-restrictive and explanatory only, with the scope of the disclosed embodiments. The ingredient amounts in the compositions/formulas described below are expressed in % by weight, based on the total weight of the composition. In all cases, the balance of the formulas was water.

Example 1—Film Properties

Several formulas were prepared according to the tables below.

Film plating: A latex film was obtained by allowing a 30 g water solution containing 4 g of the latex+APTES (active solid amount) at various ratios to dry slowly in a 100 ml PFA Petri dish (100 mm diameter×15 mm height) at room temperature for at least 3 days.

Film measurement: The latex film, with known dimensions (length, width, thickness), was mounted on the Q800 Dynamic Mechanical Analysis from TA Instrument, and tested in a DMA Temperature Ramp mode. The data was obtained using the following procedure/settings:

Equilibrate: 10° C.
Isothermal: 2 min
Ramp Rate: 3° C./min
Final Temperature: 150° C.

The storage modulus is obtained from the curve at 25° C. A high storage modulus represents a hard film, a lower modulus represents a softer film. A higher storage modulus may be associated with a better hold as a hair styling agent. The results of the test are shown in Tables 1-3 below.

TABLE 1

|  | Syntran ® PC5500[1] (g of active) | APTES[2] (g of active) | Storage Modulus (Mpa) |
|---|---|---|---|
| Ex. 1A (Comparative) | Syntran ® PC5500 only | 4 | 0 | 605.8 |
| Ex. 1B (Inventive) | 3:1 | 3 | 1 | 1361 |
| Ex. 1C (Comparative) | APTES only | 0 | 4 | Too brittle to be measured |

[1]Polyquaternium-91 (and) polyacrylate-15
[2]Aminopropyl Triethoxysilane

TABLE 2

|  | Syntran ® PC5330[1] (g of active) | APTES[2] (g of active) | Storage Modulus (Mpa) |
|---|---|---|---|
| Ex. 1D (Comparative) | Syntran ® PC5330 only | 4 | 0 | 498.5 |
| Ex. 1E (Inventive) | 5:1 | 3.33 | 0.67 | 784.2 |
| Ex. 1F (Comparative) | APTES only | — | — | Too brittle to be measured |

[1]Polyquaternium-91 (and) polyacrylate-15
[2]Aminopropyl Triethoxysilane

TABLE 3

|  | Syntran ® PC5775[1] (g of active) | APTES[2] (g of active) | Storage Modulus (Mpa) |
|---|---|---|---|
| Ex. 1G (Comparative) | Syntrane ® PC5775 only | 4 | 0 | 86.4 |
| Ex. 1H (Inventive) | 5:1 | 3.33 | 0.67 | 235 |
| Ex. 1I (Inventive) | 2:1 | 2.67 | 1.33 | 464.5 |
| Ex. 1J (Comparative) | APTES only |  |  | Too brittle to be measured |

[1]Acrylates/Ethylhexyl acrylate/HEMA copolymer (and) acrylates/Diethylaminoethylacrylate/Ethylhexylacrylate copolymer
[2]Aminopropyl Triethoxysilane As seen from Tables 1-3, the inventive formulas always displayed the highest storage modulus without being too brittle.

Example 2—High Humidity Curl Retention (HHCR)

Four formulas were prepared as shown in Table 4. In 2A contained only an acrylic copolymer active. 2B-D contained the same acrylic copolymer, but neutralized with aminomethyl propanol (AMP) and/or APTES.

Hair Treatment: Bleached hair swatches (from HIP, 14.5 cm long, about 0.5 g) were treated with a solution of the formulas (0.5 g solution/g hair). The hair was combed until the solution uniformly distributed over the hair swatch surface. The treated hair was then rolled onto a spiral rod (0.5 in diameter) and allowed to dry at room temperature overnight to provide coiled hair.

Curl Retention Measurement: The coiled hair was removed from the rod and placed in the humidity chamber at 90% relative humidity, 25° C. for 24 hours. The Curl Retention was calculated as: $(Lo-Lf)/(Lo-Li)\times 100$, wherein Lo=Fully extended hair length (14.5 cm), Li=Initial coiled hair length before humidity exposure, and Lf=Final hair length after 24 hour exposure.

TABLE 4

|  |  | Dermacryl ® AQF[1] (% of actives) | AMP % of actives) | APTES[2] % of actives) | HHCR (%) |
|---|---|---|---|---|---|
| 2A (Comparative) | Dermacryl ® AQF[1] | 2 | 0 | 0 | 36.9 |
| 2B (Comparative) | 100% Neut. With AMP | 2 | 0.28 | 0 | 54.02 |

TABLE 4-continued

| | | Dermacryl® AQF[1] (% of actives) | AMP % of actives | APTES[2] % of actives | HHCR (%) |
|---|---|---|---|---|---|
| 2C (Inventive) | 100% Neut. by 30% AMP + 70% APTES | 2 | 0.08 | 0.49 | 71.11 |
| 2D (Inventive) | 100% Neut. by APTES | 2 | 0 | 0.7 | Not measurable in simplex water system |

[1]Acrylic Copolymer
[2]APTES = 3-aminopropyltriethoxysilane

The results indicate that the neutralized latex solution has better curl retention at high humidity than non-neutralized latex. The use of APTES as co-neutralizer further enhanced the curl retention. APTES as the sole neutralization agent was not measurable due to a stability problem in a simplex water system. It is thought that stability could be restored by use of additional ingredients (e.g., thickeners), with the formula still demonstrating good high humidity curl retention properties.

Example 3—Anti-Frizz Properties after Blow Dry Application

Frizzy hair swatches were washed with a shampoo. 0.1 g of the formulas shown in the table below were applied to the hair. The swatches were then blow-dried for 45 seconds. Ease of brushing was evaluated on a scale of 1-5, with 1 denoting most difficult to brush and 5 denoting easiest to brush. The swatches were then placed in a humidity chamber for 5 hours (90% relative humidity at 40° C.). Frizz control was then evaluated, also on a scale of 1-5, with 1 denoting worst frizz control and 5 denoting best frizz control. The results are also shown in Table 5 below.

TABLE 5

| | Syntran® PC5330[1] (% of actives) | Neutralized APTES[2] (% of APTES) | Ease of brushing (1-5) | Frizz Cont. (1-5) |
|---|---|---|---|---|
| 3A (Comparative) | 2.5 | 0 | 5 | 2 |
| 3B (Comparative) | 0 | 2.5 | 2 | 1 |
| 3C (Inventive) | 2 | 0.5 | 5 | 4 |

[1]Polyquaternium-91 (and) Polyacrylate-15
[2]APTES = 3-aminopropyltriethoxysilane As seen from the table, hair treated with the inventive composition displayed a synergistic effect with respect to frizz control when compared to hair treated with either material alone.

Example 4—Anti-Frizz Properties after Air Dry Application

Frizzy hair swatches were washed with a shampoo. Each of the formulas shown in the table below were applied to the hair (0.05 g/g of hair). Ease of distribution of the solution on the swatch was evaluated on a scale of 1-5, with 1 denoting most difficult and 5 denoting easiest. The swatches were then allowed to dry overnight. The swatches were then placed in a humidity chamber for 5 hours (90% relative humidity at 40° C.). Frizz control was then evaluated, also on a scale of 1-5, with 1 denoting worst frizz control and 5 denoting best frizz control. The results are also shown in Table 6 below.

TABLE 6

| | Syntran® PC5330[1] (% of actives) | Neutralized APTES[2] (% of APTES) | Ease of Distribution | Frizz Cont. (1-5) |
|---|---|---|---|---|
| 4A (Comparative) | 2.5 | 0 | 5 | 2 |
| 4B (Comparative) | 0 | 2.5 | 2 | 1 |
| 4C (Inventive) | 2 | 0.5 | 5 | 4 |

[1]Polyquaternium-91 (and) Polyacrylate-15
[2]APTES = 3-aminopropyltriethoxysilane As seen from the table, hair treated with the inventive composition displayed a synergistic effect with respect to frizz control when compared to hair treated with either material alone.

Example 5—Adhesion

Seven formulas according to the below table were prepared, each having a total of 2.5 wt. % active. The same amount of each formula was poured into a polypropylene weigh boat (which has a similar surface energy to that of hair). The films were then peeled and assigned an adhesion value. The adhesion value corresponds to the difficulty of peeling the films (with 1 being the easiest and 5 being the hardest). Ease of brushing and frizz control were also evaluated in the same manner as in Examples 3-4. The results are also shown in Table 7 below.

TABLE 7

| | Latex(es) | Neutralized APTES[1] | Adhesion | Ease of brush | Frizz Cont. |
|---|---|---|---|---|---|
| 5A (Comparative) | 2.5% Syntran® PC5330[2] | — | 1 | 5 | 2 |
| 5B (Comparative) | 2.5% Daitosol 5000AD[3] | — | 5 | 1 | 2 |
| 5C (Comparative) | — | 2.5% | 3 | 2 | 1 |
| 5D (Inventive) | 2% Syntran® PC5330[2] | 0.5% | 2 | 5 | 4 |
| 5E (Comparative) | 2% Daitosol 5000AD[3] | 0.5% | 3 | 1 | 3 |
| 5F (Comparative) | 1.25% Syntran® PC5330[2] + 1.25% Daitosol 5000AD[3] | — | 3 | 5 | 3 |

TABLE 7-continued

| | Latex(es) | Neutralized APTES [1] | Adhesion | Ease of brush | Frizz Cont. |
|---|---|---|---|---|---|
| 5G (Inventive) | 1% Syntran ® PC5330[2] + 0.5% Daitosol 5000AD[3] | 0.5% | 5 | 5 | 5 |

[1] APTES = 3-aminopropyltriethoxysilane
[2] Polyquaternium-91 (and) Polyacrylate-15
[3] Acrylates copolymer As seen in the table, the two inventive formulas outperformed better than any other combination of ingredients with respect to frizz control. Additionally, the use of the non-ionic latex in Example 5G further improved the adhesion on the substrate.

Example 6—Adhesion

Seven formulas according to the below table were prepared, each having a total of 2.5 wt. % active, and tested for adhesion according to Example 5. Ease of brushing and frizz control were also evaluated in the same manner as in Examples 3-4. The results are also shown in Table 8 below.

TABLE 8

| | Latex(es) | Neutralized ARIES [1] | Adhesion | Ease of brush | Frizz Cont. |
|---|---|---|---|---|---|
| 6A (Comparative) | 2.5% Syntran ® PC5330[2] | — | 1 | 5 | 2 |
| 6B (Comparative) | 2.5% Daitosol 5000STY[3] | — | 4 | 1 | 2 |
| 6C (Comparative) | — | 2.5% | 3 | 2 | 1 |
| 6D (Inventive) | 2% Syntran ® PC5330[2] | 0.5% | 2 | 5 | 3 |
| 6E (Comparative) | 2% Daitosol 5000STY[3] | 0.5% | 3 | 1 | 3 |
| 6F (Comparative) | 1.25% Syntran ® PC5330[2] + 1.25% Daitosol 5000STY[3] | — | 3 | 5 | 3 |
| 6G (Inventive) | 1% Syntran ® PC5330[2] + 0.5% Daitosol 5000STY[3] | 0.5% | 4 | 5 | 5 |

[1] APTES = 3-aminopropyltriethoxysilane
[2] Polyquaternium-91 (and) Polyacrylate-15
[3] Styrene/Acrylates Copolymer As seen in the table, the two inventive formulas performed well in each parameter. Additionally, the use of the non-ionic latex in Example 6G outperformed any of the of the other formulas with respect to frizz control.

What is claimed is:

1. A hair styling composition comprising:
   a. about 0.01 to about 10%, by weight of the total composition, of 3-aminopropyltriethoxysilane; and
   b. about 0.1 to about 20%, by weight of the total composition, of polyacrylate-15.
2. The hair styling composition of claim 1, further comprising styrene/acrylates copolymer.
3. The hair styling composition of claim 2, wherein the styrene/acrylates copolymer is present in an amount of from about 0.1 to about 10% by weight of the total composition.
4. The hair styling composition of claim 1, further comprising a plasticizer.
5. The hair styling composition of claim 1, wherein the composition does not further comprise an acid.
6. A method of styling hair, the method comprising applying the hair styling composition of claim 1 to hair.
7. The method of claim 6, further comprising shaping the hair.

* * * * *